United States Patent [19]

Meyer

[11] Patent Number: 5,616,128
[45] Date of Patent: Apr. 1, 1997

[54] SELF-INJECTION DEVICE

[75] Inventor: Philippe Meyer, Grienbachstrasse, Switzerland

[73] Assignee: MED-Plastic AG, Switzerland

[21] Appl. No.: 302,847

[22] PCT Filed: Jan. 27, 1993

[86] PCT No.: PCT/EP93/00180

§ 371 Date: Nov. 7, 1994

§ 102(e) Date: Nov. 7, 1994

[87] PCT Pub. No.: WO94/16752

PCT Pub. Date: Aug. 4, 1994

[51] Int. Cl.⁶ ..................................................... A61M 5/20
[52] U.S. Cl. ............................................... 604/139; 604/51
[58] Field of Search ............................. 604/51, 93, 139, 604/184, 197, 201, 218

[56] References Cited

U.S. PATENT DOCUMENTS

| | | | |
|---|---|---|---|
| 2,408,323 | 9/1946 | Lockhart | 604/201 X |
| 3,320,955 | 5/1967 | Sarnoff. | |
| 3,742,948 | 7/1973 | Post et al. | 604/139 |
| 3,943,327 | 3/1976 | Vizelyi et al.. | |
| 3,977,402 | 8/1976 | Pike | 604/51 |
| 4,178,928 | 12/1979 | Tischlinger | 604/139 |
| 4,258,713 | 3/1981 | Wardlaw | 604/139 |
| 4,624,660 | 11/1986 | Mijers et al.. | |
| 4,968,302 | 11/1990 | Schluter et al. | 604/139 X |
| 5,238,927 | 8/1993 | Brown et al. | 604/51 X |
| 5,391,151 | 2/1995 | Wilmot | 604/139 |

FOREIGN PATENT DOCUMENTS

| 107874 | 10/1983 | European Pat. Off.. |
|---|---|---|
| 1094932 | 9/1954 | Germany. |

Primary Examiner—Sam Rimell
Attorney, Agent, or Firm—Brumbaugh, Graves, Donohue & Raymond

[57] ABSTRACT

A self-injection device has a tubular sleeve which is open at its posterior end and partially closed at its anterior end. An ampule sealed at its posterior end by a piston and at its anterior end by a membrane is axially arranged within the tubular sleeve. An injection needle having a terminal flange at its posterior end and an anterior end for piercing the membrane is axially arranged in the ampule. A tubular actuating cap having a piston rod emanating from the bottom of cap for acting upon the piston is slidably guided on the sleeve. The actuating cap and the piston rod are traversed by a central bore having axially extending grooves. The device also includes a locking pin having radially projecting spring tongues. A first segment of the spring tongue extends in an axial direction on the periphery of the locking pin and a second segment is bent at an obtuse angle, extending obliquely outward in a radial-axial direction through the axially extending grooves in the central bore. When fully inserted into the device, the spring tongues contact the posterior end of the sleeve to prevent unintentional triggering of the injection needle.

19 Claims, 4 Drawing Sheets

SELF-INJECTION DEVICE

The invention relates to a self-injection device having a tubular sleeve in which an ampule is axially arranged and which is closed off by a membrane at the anterior end and by a piston at the posterior end, and having an injection needle guided axially displaceable in the ampule, configured to puncture the membrane and for injection at the anterior end, and in contact with the piston by way of a terminal flange at the posterior end.

However, the invention may also be applied to self-injection devices comprising a tubular sleeve in which an ampule is guided axially displaceable and which is closed off by a membrane at the anterior end and by a piston at the posterior end, and further comprising an injection needle guided axially displaceable in the sleeve ahead of the ampule and configured for injection at the anterior end and to puncture the membrane at the posterior end.

Such devices serve chiefly for emergency medication such as antidotes. For this purpose, the device must be ready for instant use, absolutely trouble-free in operation, and ensuring sterility of the medication contained and of the enclosed needle over a long period.

German Patent 1,094,932, U.S. Pat. No. 3,320,955, U.S. Pat. No. 4,624,660 and European Patent 0,107,874 disclose devices of the kinds initially mentioned in which the advance of the injection needle from the sleeve and the advance of the piston in the ampule are effected by spring action. Thus the piston is acted upon by a piston rod engaged at the posterior end of the device by several snap hooks in an axial aperture of a rear wall of the sleeve and prestressed by a strong spring slipped over the piston rod and tending to propel it forward. The spread of the snap hook of the piston rod at the posterior end of the sleeve is secured by a locking pin introduced from the rear centrally between the snap hook catching the rim of the hole in the rear wall of the sleeve. To trigger the injection, first the locking pin is pulled away axially towards the rear, and then, by slight displacement of an actuating sleeve slipped over the main sleeve and having projections on the inside for the purpose, the snap hooks of the piston rod are pinched together. Since the snap hooks no longer engage the edges of the opening, the suspension of the piston rod in the sleeve is released, and the spring drives the piston rod forward. By the forward motion of the piston rod, in the kind of device first mentioned the injection needle simultaneously punctures the ampule membrane, and during the advance of the piston and injection needle, delivers the medication contained in the ampule into the body. In the second kind of device initially mentioned, the advance of the piston first effects an advance of the entire ampule and of the injection needle arranged ahead of it until the latter has entered the body, and then a puncture of the ampule membrane by the posterior end of the needle, and finally an advance of the piston in the ampule with simultaneous expulsion of the medication through the needle into the body.

So in these known devices the process of injection is fully automatic after removal of the locking pin, if the actuating sleeve is shifted slightly relative to the inner sleeve for triggering, i.e. if the actuating sleeve is grasped and pressed against a body part, since this brings the inner sleeve into contact with the body part and shifts it slightly relative to the actuating sleeve. The process of injection then occurs instantaneously. This triggering method, however, has the disadvantage that after removal of the locking pin, the automatic injection will be brought about even by slight concussions, impacts or dropping of the device, spilling the medication and rendering the device worthless. The known devices therefore fall short of the requirement of absolutely trouble-free operation under the most adverse conditions, such as typify emergency use.

The object of the invention is to improve devices of the kind initially mentioned in such a manner that an unintentional triggering can be ruled out, and that at the same time a simple manipulation while maintaining readiness for instant use and assurance of sterility will be possible. This object is accomplished, according to the invention, in that a tubular actuating cap is displaceably guided on the sleeve at the posterior end and is secured against being pulled off, comprising a piston rod emanating from the bottom of the cap, introduced into the sleeve and acting on the piston, the bottom of the cap and the piston rod being traversed by a central bore into which, in the starting position with cap partly slipped over the sleeve and piston rod engaging the piston, a locking pin is introduced, having radially projecting spring tongues at its introduced end that pass through lateral slits in the piston rod and rest against the rear end of the sleeve.

By virtue of this novel actuating and locking mechanism, the actuating cap must be intentionally shifted in order to effect the injection. Unintentional triggering by concussions, impact etc., as in the known devices, is precluded. The configuration of the locking pin according to the invention affords extremely simple manipulation, in that the locking pin need merely be pulled away to the rear in order to render the device ready for use. The injection itself is brought about by grasping the actuating cap and pressing the entire device against a part while at the same time advancing the actuating cap. This has the further advantage that the entire maneuver is performed in the same way as with the known devices, i.e. no retraining is necessary for use, and dependability of use is secured by the accustomed procedure.

It should be mentioned that U.S. Pat. No. 3,943,927, for an injection device of a different kind, discloses the provision of a tubular actuating cap of the configuration portrayed.

In advantageous modification of the invention, axially extending grooves are provided on the inside of the central bore, their number and circumferential distribution matching those of the tongues on the locking pin. Both when introducing and when withdrawing the locking pin, these grooves serve as slide guides for the tongues, thereby facilitating assembly of the device as well as its manipulation for the intended purpose.

It is especially advantageous for the tongues at the periphery of the locking pin to extend in axial direction within a first linear segment and project beyond the locking pin, and then, in a second linear segment diverted at an obtuse angle, pass obliquely outward in radial-axial direction. Since the tongues are made of elastic material, this configuration of the tongues makes possible a compression of the tongues in ideal manner, so that they may be introduced and pulled by way of the central bore.

It is favorable also for the ends of the tongues to be turned outward in radial direction and engage recesses on the inside of the actuating cap, thus affording an additional locking effect.

In all conformations according to the invention, it is advantageous for the uninserted end of the locking pin to comprise a grip portion of diameter greater than the diameter of the central bore. In this way, the locking pin is additionally fixed, so that especially with use of the recesses on the inside of the actuating cap, the locking pin is fixed in position in both directions. Also, the grip portion permits convenient manipulation.

In an especially preferred embodiment of the invention, the posterior end walls of the slits in the piston rod are beveled, the edges of the beveled end walls of the slits lying farther posterior being located on the inside of the bore. This facilitates engagement and disengagement of the tongues entering the slits.

A simplified structure compared to the known devices of the second kind and an improved sterility will result if the posterior end of the injection needle is guided, in manner known per se, by a needle guide piston displaceably lodged in the sleeve, projects beyond the same, and is fixed therein, and if this projecting end of the needle is covered by an elastic protective cap serving as spacer spring, or sealingly connected to the ampule by an elastic protective conduit serving as spacer spring.

Other features and advantages of the invention will appear from the following description of the accompanying drawings, in which FIG. 1 shows a longitudinal section of a device of the first kind configured according to the invention;

Figure 1:
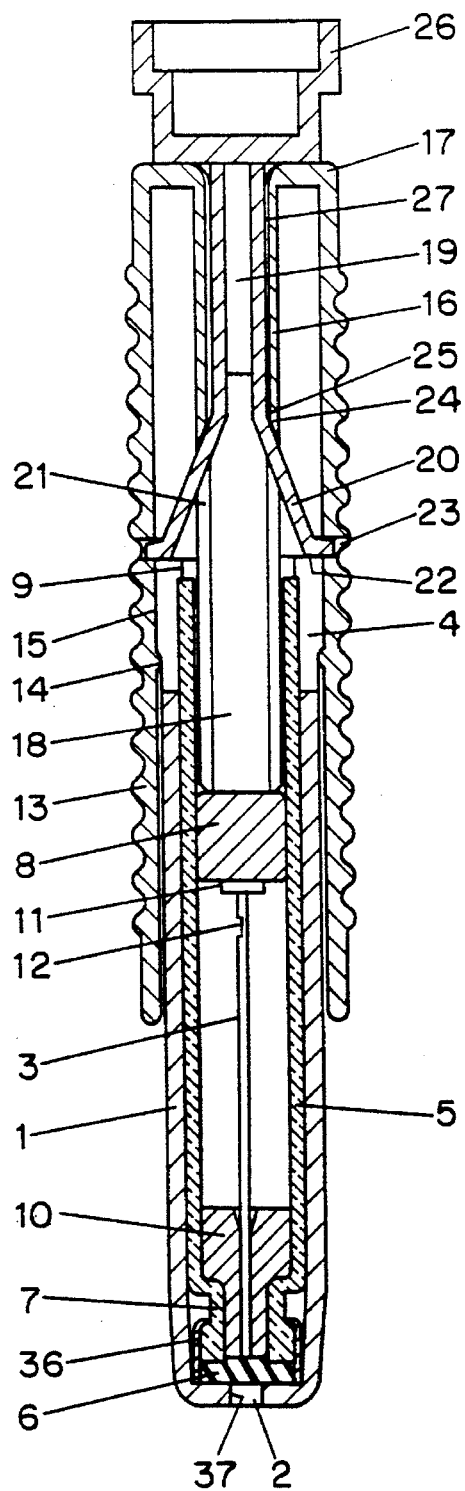

According to FIG. 1, a first kind of device for self injection comprises a tubular sleeve 1 having at its anterior end an opening 2 of small diameter for passage of an injection needle 3 and substantially open at the posterior end 4. In the sleeve 1, an ampule 5 of glass or metal, for example a standard glass ampule, is arranged. The ampule 5 is closed at the anterior end by a disk-shaped membrane 6 of rubber for example, held to the neck of the ampule by an aluminum cap 36 with central opening 37 pressed upon the neck 7 of the ampule. At the posterior end, the ampule 5 is closed off by a piston 8, for example a rubber plug, sealingly slidable in the ampule. At the anterior end, the ampule 5 is in contact by way of the membrane 6 with the inside of the anterior end wall of the sleeve 1 and is fixed therein at its posterior end by a turned-in rim 9 of the sleeve 1.

The injection needle 3 is slidably lodged in the ampule 5, namely in a needle guide 10 filling out the anterior portion of the ampule and having a central bore for sliding lodgment of the needle 3. The needle 3 is pointed in conventional manner at the anterior end to puncture the membrane 6 and for injection, and has a flange 11 at its posterior end, whereby it makes contact with the piston 8. Besides, the needle bore, not shown, is in communication with the anterior of the ampule by way of a side opening 12 in the posterior portion of the needle. Through this opening 12, upon entry of the piston 8 into the ampule 5, the medication contained in the ampule is expelled through the bore of the needle and injected.

Figure 2:
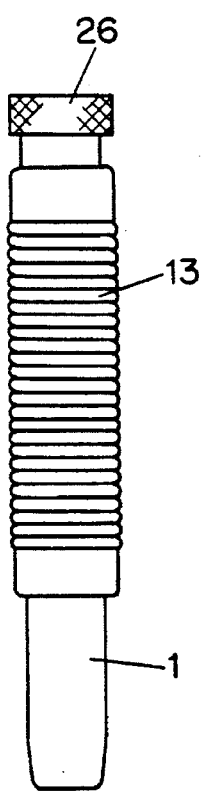
FIG. 2 shows a reduced outside view of the device of FIG. 1.
Figure 3:
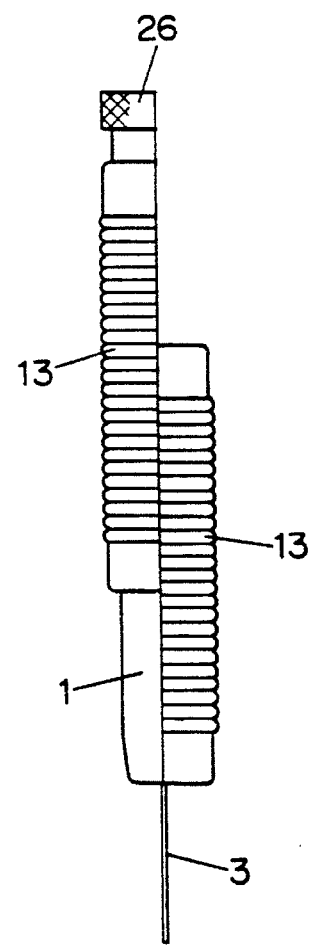
FIG. 3 shows a reduced outside view of the device of FIG. 1, half in each of two different actuating positions.

The piston 8 is actuated by the following arrangement. At the posterior end of the sleeve, a tubular actuating cap 13 is slidably guided on the sleeve 1 and secured against being pulled off by a projection 14 arranged on the inside of the cap and cooperating with a corresponding projection 15 on the outside of the posterior end 4 of the sleeve. The actuating cap 13 is shown in more detail in FIGS. 7 to 10. The length of the actuating cap 13 in relation to the length of the sleeve 1 and the arrangement of the projections 14, 15 are so chosen that upon*displacement of the actuating cap from the position shown in the left-hand half of FIG. 3 to the position shown in the right-hand half of FIG. 3 corresponds to the distance to be traversed by the piston 8 in order to expel the medicinal dose contained in the ampule 5. The outside of the actuating cap 13, as may be seen in FIGS. 2 and 3, is grooved to provide a fingerhold.
*[bei einer 'upon' may be read eine 'a' for syntax]

The actuating cap 13 is fixedly connected to a piston rod 16 acting on the piston 8 and protruding out from the bottom 17 of the actuating cap 13 in axial direction into the interior of the cap, being of such diameter that it may be introduced into the ampule 5 from its posterior end. The piston rod 16 and the bottom 17 of the cap are traversed by a common central axial bore 18, so that the Diston rod 16 may alternatively be regarded as a tube, or the entire arrangement of actuating cap 13 and piston rod 16 as a double-jacketed tube closed at one end.

Figure 11:
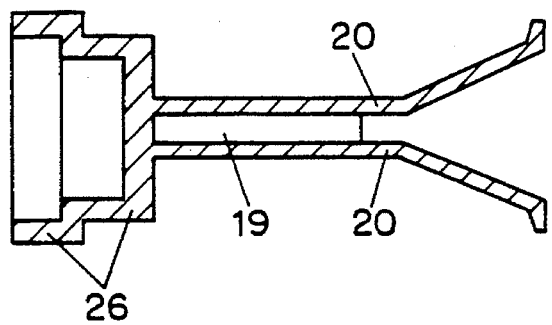
FIG. 11 shows the locking pin with grip portion and tongues deployed, in longitudinal section.
Figure 12:
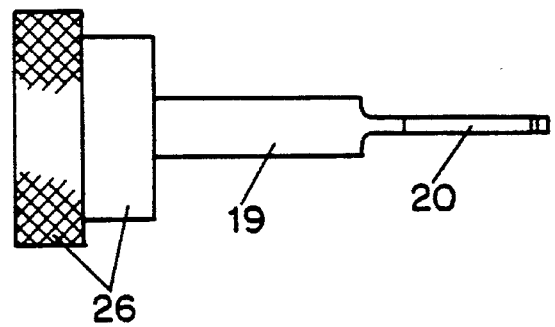
FIG. 12 shows a view of the locking pin with grip portion and tongue in a position rotated 90° relative to FIG. 11.
Figure 13:
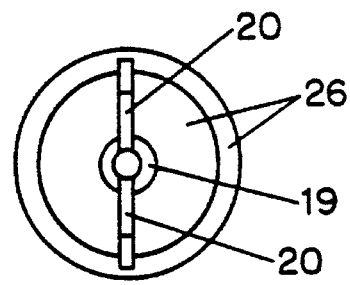
FIG. 13 shows the locking pin with grip portion and tongue in end view from in front.

Into the bore 18, a locking pin 19 is introducible, and removable from the bore again to unlock the device. This locking pin is shown in more detail in FIGS. 11 to 13, and comprises two spring tongues 20 mutually opposed and extending in axial direction on its periphery, traversing the lateral slits 21 in the piston rod 16 and making contact at their ends with the posterior end 22 of the sleeve 1. These tongues 20, in a first linear segment, run in axial direction on the periphery of the locking pin 13 and beyond it, then bent at an obtuse angle and run obliquely outward in radial-axial direction in a second linear segment. At their end, the tongues are turned outward in radial direction and catch in recesses 23 on the inside of the actuating cap 13. At least these tongues 20 of the locking pin 19 are made of elastic material, and are therefore compressible during introduction or extraction of the locking pin into or out of the bore 18, as the case may be, will spring apart upon reaching the slits 21, and catch in recesses 23 of the actuating cap 13 in the position shown in FIG. 1. The catching of the spring tongues 20 in this position is facilitated by the beveling of the posterior end walls 24 of the slits 21, the more posterior edges 25 of these beveled end walls 24 being the ones located on the inside of the bore 18.

The posterior end of the locking pin 19 comprises a grip portion 26 of diameter greater than the diameter of the central bore 18.

To unlock the device, the locking pin 19 is pulled away rearward in axial direction with the aid of the grip portion 26, the ends of the tongues 20 first disengaging from the recesses 23 and then the entire tongues 20 press towards each other until they are approximately parallel and can be pulled away through the bore 18 together with the pin 19.

On the inside of the central bore 18, grooves 27 extending axially are provided, their number and circumferential distribution corresponding to the number and circumferential distribution of the tongues 20 on the locking pin 19. Hence the tongues 20 slide in these grooves during insertion and extraction of the locking pin 19.

For the injection itself, after pulling away the locking pin 19, the entire device is placed in contact by its anterior end with a body part, generally the thigh, and the actuating cap 13 is thrust forward, whereby the piston 8 and simultaneously the injection needle 3 are pushed forward by way of the piston rod 16; the needle punctures the membrane 6, and during its penetration into the body, injection of the medication contained in the ampule 5 is made possible by way of the opening 12.

Figure 4:
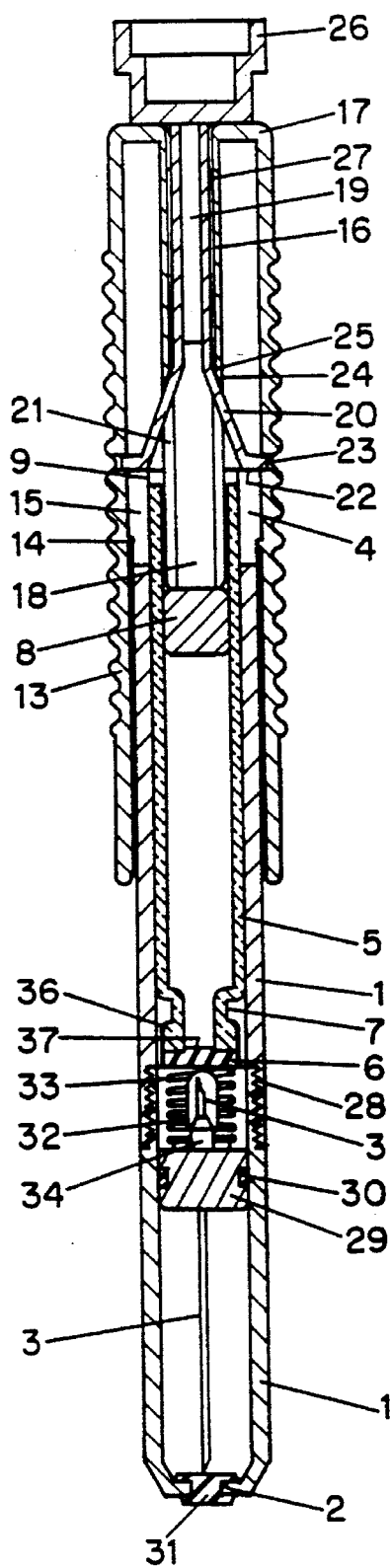
FIG. 4 shows a device of the second kind configured in accordance with the invention, in longitudinal section.
Figure 5:
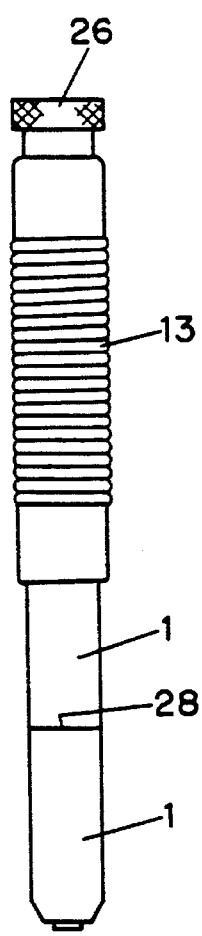
FIG. 5 shows a reduced outside view of the device of FIG. 4.
Figure 6:
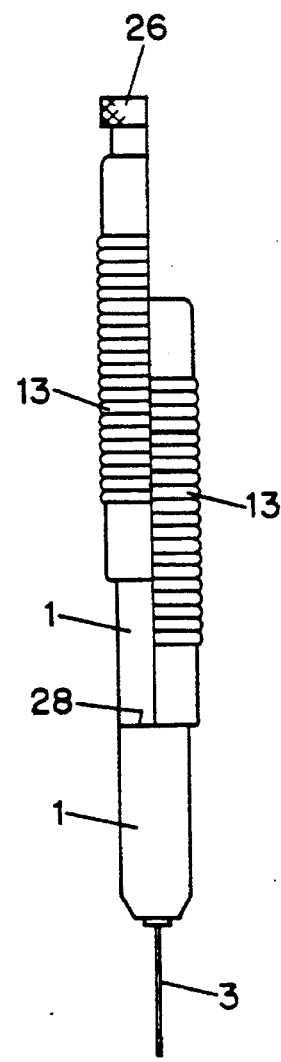
FIG. 6 shows a reduced outside view of the device according to FIG. 4, half in each of two different actuating positions.
Figure 7:
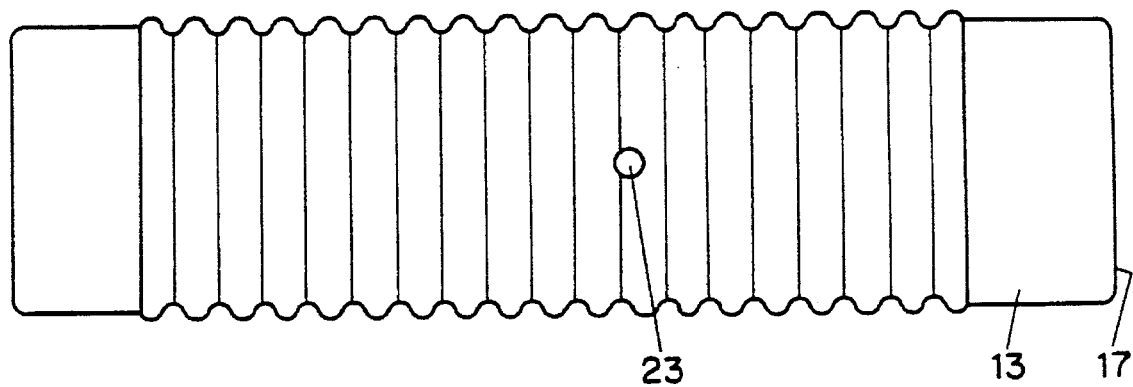
FIG. 7 shows a view in detail of the actuating cap according to the invention.
Figure 8:
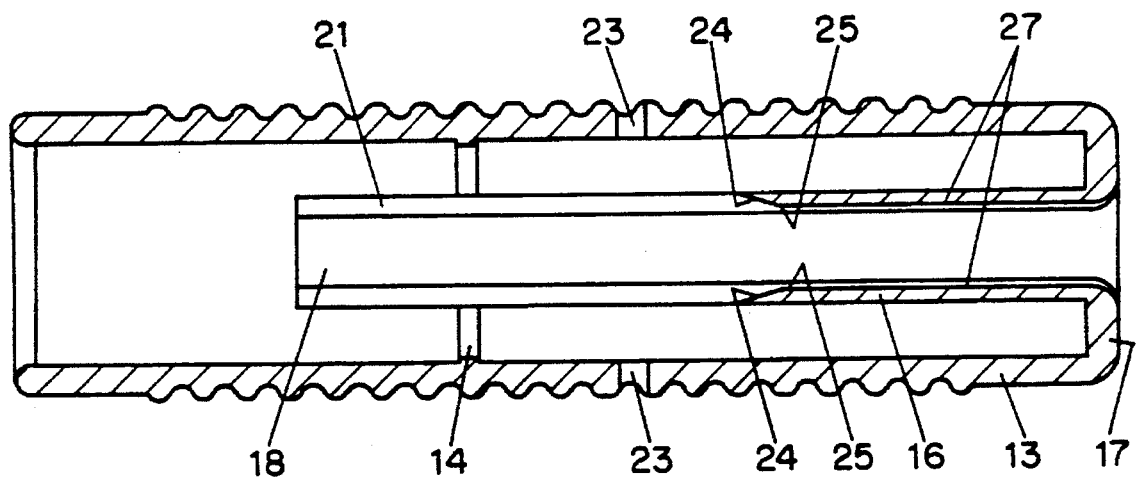
FIG. 8 shows the actuating cap of FIG. 7 in longitudinal section.
Figure 9:
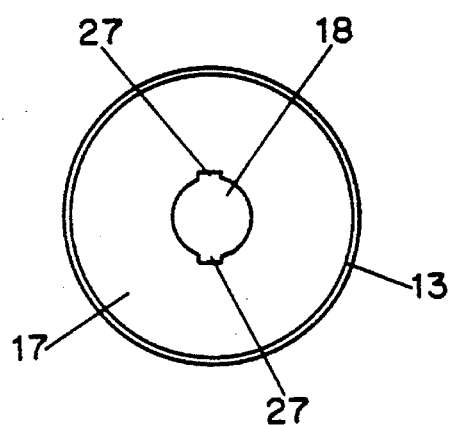
FIG. 9 shows the actuating cap in end view from behind.
Figure 10:
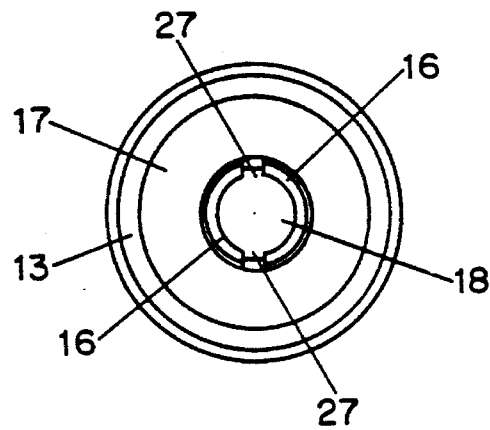
FIG. 10 shows the actuating cap in end view from the front.

FIGS. 4 to 6 show a second kind of the self-injection device, likewise configured in accordance with the invention. The unlocking and actuating mechanism is of exactly the same structure as in the embodiment of FIGS. 1 to 3, and so corresponding parts have been marked with the same reference numerals. The only difference consists in the injection mechanism proper, which is described below.

In this embodiment, the sleeve 1 is longer and contains the injection needle 3 and the ampule 5 in tandem. For assembly purposes, the sleeve 1 consists of two parts, screwed together by means of a thread at their junction 28. The ampule 5 is slidably lodged in the sleeve 1. As before, the ampule 5 is closed off at its anterior end by the membrane 6, held on the neck 7 of the ampule by the open aluminum cap 36, and at the posterior end the ampule is closed off by the piston 8. In front of the ampule 5 the injection needle 3 is arranged, passed through a needle guide piston 29 and fixed therein, which piston is located in the region of the posterior end of the needle 3. The needle guide piston 29 is guided in sliding seal by way of an O-ring 30 on the inside of the sleeve 1. The anterior opening 2 of the sleeve 1 is closed by a protective membrane 31. The end of the needle 3 projecting behind the needle guide piston 29 is provided with a flange 34 and covered with a soft rubber protective cap 32 inverted over this flange. Slipped over the protective cap 32 and fixed to the needle guide piston 29, a spacer spring 33 is arranged, holding the needle guide piston and hence the posterior end of the needle 3 at such a distance from the membrane 6 closing off the ampule 5 that in the absence of force acting on the spring 33, the posterior sharpened end of the needle 3 will not puncture its protective cap 32, nor will the protective cap 32 touch the ampule membrane 6.

The spacer spring 33 must also be so dimensioned that upon actuation of the actuating cap 13 and consequent displacement of the piston 8 by the piston rod 16, the ampule 5 will at first be picked up and advanced by friction between the piston 8 and the inside of the ampule. Thus the ampule 5, by way of the spacer spring 33, will advance the needle guide piston 29 with the needle 3, rupturing the protective membrane 31, until the needle guide piston 29 encounters the inside of the anterior wall of the sleeve 1. Only upon continued action on the piston 8 will the spacer spring 33 be compressed, whereupon the posterior end of the needle pierces the protective cap 32 and the needle membrane 6. This establishes communication between the interior of the ampule and the body tissue, and finally the piston 8, upon further action thereon, enters the ampule 9 and expels the medication contained in the ampule by way of the injection passage.

The somewhat greater structural length of this embodiment is compensated by the advantage that standardized glass ampules may be used, without need first to mount a special needle and a special needle guide as in the embodiment of FIG. 1. Besides, in this embodiment the injection of the medication does not occur until after the injection needle 3 has fully entered the body, whereas in the first embodiment, the penetration of the needle and the injection take place simultaneously.

Figure 14:
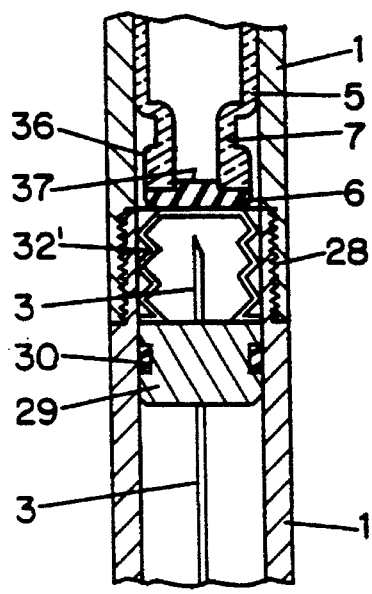
FIGS. 14 to 16 each show a segment of FIG. 4 with additional details of the device according to the invention in sectional view.
Figure 15:
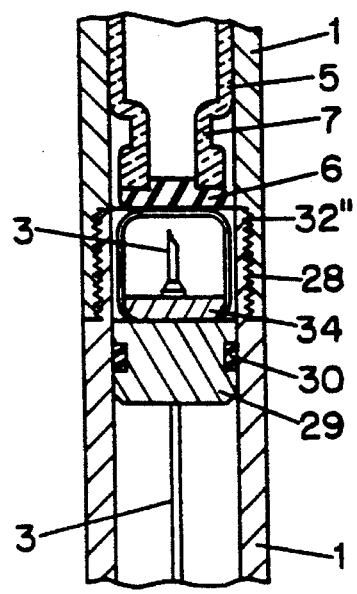
Figure 16:
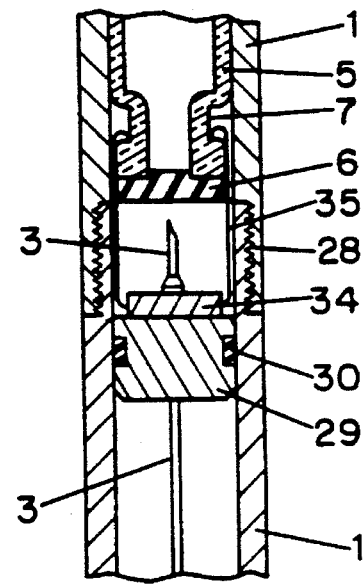

Instead of the use of a spacer spring 33, the protective cap 32 itself may act as a spring. FIG. 14 shows a protective cap 32' configured as a plastic bellows, sealingly welded or bonded to the needle guide piston 29 and in contact with the ampule membrane 6. The protective cap 32" shown in FIG. 15 is made of silicone rubber and also exhibits a suitable resistance to deformation, replacing the spacer spring 33. FIG. 16 shows an especially advantageous modification in which, instead of a protective cap, a protective hose 35 is connected at one end to the needle guide piston 29 and at the other end sealingly to the neck 7 of the ampule. Again, the resistance of the protective hose 35 to deformation is so chosen as to replace the force of the spacer spring 33. It will be understood that the deformation properties of the modified protective caps 32' and 32" and of the protective hose 35 must be chosen in the same manner as the spring properties of the spacer spring 33.

I claim:

1. A self-injection device comprising:

a tubular sleeve open at the posterior end thereof and partially closed at the anterior end thereof;

an ampule axially arranged within said tubular sleeve, said ampule being sealed at the posterior end thereof by a piston and sealed at the anterior end thereof by a membrane;

an injection needle axially arranged within said ampule, said needle having a terminal flange at its posterior end for contacting the piston and an anterior end for piercing the membrane;

a tubular actuating cap guided on the tubular sleeve having a piston rod emanating from the bottom of the cap for acting upon the piston, the actuating cap and the piston rod being traversed by a central bore having axially extending grooves;

means for preventing the tubular actuating cap from being removed from the posterior end of the tubular sleeve; and a locking pin comprising radially projecting spring tongues, each tongue having a first segment extending in an axial direction on the periphery of the locking pin and a second segment bent at an obtuse angle, extending obliquely outward in a radial-axial direction through the axially extending grooves in the central bore for contacting the posterior end of the sleeve, wherein the locking pin is insertible into the central bore for preventing unintentional triggering of the injection needle.

2. The self-injection device of claim 1, wherein the ends of the spring tongues extend radially outward and engage recesses located on the inside of the actuating cap.

3. The self-injection device of claim 2, wherein the posterior end of the locking pin comprises a grip portion having a diameter which is greater than the diameter of the central bore.

4. The self-injection device of claim 3, wherein the piston rod includes slits having posterior end walls which are beveled.

5. The self-injection device of claim 4, wherein the posterior edges of the beveled end walls are located on the inside of the central bore.

6. The self-injection device of claim 1, wherein the means for preventing the tubular actuating cap from being pulled off from the posterior end of the tubular sleeve comprises a projection arranged on the inside of the actuating cap which cooperates with a corresponding projection on the outside of the posterior end of the tubular sleeve.

7. A self-injection device comprising:

a tubular sleeve having a first portion and a second portion which portions are threadably connected, the posterior end of the tubular sleeve being open and the anterior end of the tubular sleeve being closed by a protective membrane;

an ampule axially arranged within said first sleeve portion, said ampule being sealed at the posterior end thereof by a piston and at the anterior end thereof by a membrane;

an injection needle axially arranged within said second sleeve portion;

a tubular actuating cap slidably guided on the tubular sleeve having a piston rod emanating from the bottom of the cap for acting upon the piston, the actuating cap and piston rod being traversed by a central bore having axially extending grooves;

means for preventing the tubular actuating cap from being removed from the posterior end of the tubular sleeve; and a locking pin comprising radially projecting spring tongues, each spring tongue having a first segment extending in an axial direction on the periphery of the locking pin and a second segment bent at an obtuse angle, extending obliquely outward in a radial-axial direction through the axially extending grooves in the central bore for contacting the posterior end of the sleeve, wherein the locking pin is insertible into the central bore for preventing unintentional triggering of the injection needle.

8. The self-injection device of claim 7 further comprising:

a needle guide piston located near the posterior end of the needle for guiding the needle in the axial direction;

a flange provided at a posterior end of the needle projecting behind the needle guide piston;

a soft protective cap connected to the flange and formed over the posterior end of the needle projecting behind the flange; and a spacer spring positioned around the protective cap and between the needle guide piston and the protective membrane of the ampule for holding the needle guide piston at a distance from the membrane, such that in the absence of a predetermined force acting upon the spacer spring, the posterior end of the sharpened needle does not puncture the protective cap or touch the ampule membrane.

9. The self-injection device of claim 8, wherein the ends of the spring tongues extend radially outward for engaging recesses located on the inside of the actuating cap.

10. The self-injection device of claim 9, wherein the posterior end of the locking pin comprises a grip portion having a diameter which is greater than the diameter of the central bore.

11. The self-injection device of claim 10, wherein the piston rod includes slits having posterior end walls which are beveled.

12. The self-injection device of claim 11, wherein the posterior edges of the beveled end walls are located on the inside of the central bore.

13. The self-injection device of claim 7, wherein the means for preventing the tubular actuating cap from being pulled off from the posterior end of the tubular sleeve comprises a projection arranged on the inside of the actuating cap which cooperates with a corresponding projection on the outside of the posterior end of the tubular sleeve.

14. The self-injection device of claim 7 further comprising:

a needle guide piston located near the posterior end of the needle for guiding the needle in the axial direction; and an elastic protective cap covering the posterior end of the needle projecting behind the needle guide piston for serving as a spacer spring.

15. The self-injection device of claim 14, wherein the ends of the spring tongues extend radially outward for engaging recesses located on the inside of the actuating cap.

16. The self-injection device of claim 15, wherein the posterior end of the locking pin comprises a grip portion having a diameter which is greater than the diameter of the central bore.

17. The self-injection device of claim 16, wherein the piston rod includes slits having posterior end walls which are beveled.

18. The self-injection device of claim 17, wherein the posterior edges of the beveled end walls are located on the inside of the central bore.

19. The self-injection device of claim 14, wherein the means for preventing the tubular actuating cap from being pulled off from the posterior end of the tubular sleeve comprises a projection arranged on the inside of the actuating cap which cooperates with a corresponding projection on the outside of the posterior end of the tubular sleeve.

* * * * *